US005998151A

United States Patent [19]
Johnston et al.

[11] Patent Number: 5,998,151
[45] Date of Patent: Dec. 7, 1999

[54] METHODS FOR PREDICTING THE EFFICACY OF A CHEMOTHERAPEUTIC REGIMEN FOR GASTROINTESTINAL CANCERS USING ANTIBODIES SPECIFIC FOR THYMIDYLATE SYNTHASE

[75] Inventors: Patrick G. Johnston, Bethesda; Carmen J. Allegra, North Potomac, both of Md.; Edwin R. Fisher, Pittsburgh, Pa.

[73] Assignee: The United States of America as represented by the Department of Health and Human Services, Washington, D.C.

[21] Appl. No.: 08/758,034

[22] Filed: Nov. 27, 1996

Related U.S. Application Data

[60] Provisional application No. 60/007,825, Dec. 1, 1995.
[51] Int. Cl.$^6$ .............................. G01N 33/53; C07K 1/00; C07K 16/00
[52] U.S. Cl. .......................... 435/7.1; 435/7.23; 435/7.5; 435/7.92; 530/387.1; 530/391.1; 530/350
[58] Field of Search .............................. 530/387.1, 391.1, 530/350; 435/7.1, 7.23, 7.5, 7.92

[56] References Cited

PUBLICATIONS

Kevomarsi et al (J. Cell Biol. 115 (3pt2):206A, 1991.
Peters et al (J. Clin Oncol, 12:2035–2042), 1994.
Drake et A (AntiCancer Drugs 4:431–435, 1993.
Ajani, Jaffer, A., et al. (1991) "Resectable Gastric Carcinoma", *Cancer* 68(7):1501–1506.
Alexander, H. Richard, et al. (1995) "Thymidylate Synthase Protein Expression", *The Cancer Journal from Scientific American*, 1(1):49–54.
Chu, Edward, et al. (1990) "Interaction of γ Interferon and 5–Fluorouracil in the H630 Human Colon Carcinoma Cell Line", *Cancer Research* 50:5834–5840.
Elledge, R.M., et al. (1994) "Evaluation of thymidylate synthase RNA expression by polymerase chain reaction", *Molecular and Cellular Probes* 8:67–72.
Johnston, Patrick G., et al. (1991) "Production and Characterization of Monoclonal Antibodies That Localize Human Thymidylate Syntase in the Cytoplasm of Human Cells and Tissue", *Cancer Research* 51:6668–6676.
Johnston, Patrick G., et al. (1992) "Immunological Quantitation of Thymidylate Synthase Using the Monoclonal Antibody TS 106 in 5–Fluorouracil–sensitive and—resistant Human Cancer Cell Lines", *Cancer Research* 52:4306–4312.
Johnston, Patrick G., et al. (1994) "The Role of Thymidylate Synthase Expression in Prognosis and Outcome of Adjuvant Chemotherapy in Patients with Rectal Cancer", *Journal of Clinical Oncology*, 12(12):2640–2647.
Johnston, Patrick G., et al. (1995) "Thymidylate Synthase Gene and Protein Expression Correlate and Are Associated with Response to 5–Fluorouracil in Human Colorectal and Gastric Tumors", *Cancer Research* 55:1407–1412.

Kelsen, David, et al. (1992) "FAMTX Versus Etoposide, Doxorubicin, and Cisplatin: A Random Assignment Trial in Gastric Cancer", *Journal of Clinical Oncology* 10(4):541–548.
Silberman, L. Leichman, et al. (1992) "Preoperative Systemic Chemotherapy Followed by Adjuvant Postoperative Intraperitoneal Therapy for Gastric Cancer: A University of Southern California Pilot Program", *Journal of Oncology* 10(2):1933–1942.
Lerner, Adam, et al. "Etoposide, Doxorubicin, and Cisplatin Chemotherapy for Advanced Gastric Adenocarcinoma: Results of a Phase II Trial", *Journal of Oncology*, 10(4):536–540.
Romain, Sylvie, et al. (1997) "DNA–Synthesis Enzyme Activity: A Biological Tool Useful for Predicting Anti–Metabolic Drug Sensitivity in Breast Cancer?", *Int. J. Cancer (Pred. Oncol)*74:156–161.
Swain, S.M., et al. (1989) "Flurouracil and High–Dose Leucovorin in Previously Treated Patients with Metastatic Breast Cancer",*Journal of Clinical Oncology* 7(7):890–899.
Wilke, H., et al. (1989) "Preoperative Chemotherapy in Locally Advanced and Nonresectable Gastric Cancer: A Phase II Study with Etoposide, Doxorubicin, and Cisplatin", *Journal of Clinical Oncology*, 7(():1318–1326.
Keyomarsi, K., et al. (1991) "Differential Expression of Thymidylate Synthase Message Versus Protein in Synchronized Human Breast Cancer Cells",*J. Cell Biol.* 115 (3 Part 2): 206A.
Kang, Y.K. et al. (1992) "The Effect of Neoadjuvant Chemotherapy on the Surgical Outcome of Locally Advanced Gastric Adenocarcinoma: Interim Report of a Randomized Controlled Trial", *Proceedings of ASCO* 11:173 (505).
Johnston, P.G., et al. (1994) "Thymidylate Syntase Protein and Gene Expression Predicts for Response to 5–Fluorouracil Leucovorin Chemotherapy in Patients with Colorectal and Gastric Cancer", *Proceedings of ASCO* 13:196 (569).
Ajani, J.A., et al. (1992) "Preoperative and Postoperative Chemotherapy (CT) for Patients with Potentially Resectable Gastric Carcinoma", *Proceedings of ASCO* 11:165 (475).

*Primary Examiner*—Paula K. Hutzell
*Assistant Examiner*—Susan Ungar
*Attorney, Agent, or Firm*—Townsend and Townsend and Crew, LLP

[57] ABSTRACT

Methods for determining whether a chemotherapeutic treatment is appropriate for patients afflicted with gastrointestinal cancers, comprising;

(a) obtaining a solid tumor tissue sample from the patient;
(b) measuring a thymidylate synthase expression level in the tissue sample; and
(c) comparing the thymidylate synthase expression level with a group of standard tumor tissue samples, the standards having known thymidylate synthase expression levels and known responses to the chemotherapeutic treatment, to determine if that chemotherapeutic treatment is appropriate for the patient.

11 Claims, 4 Drawing Sheets

METHODS FOR PREDICTING THE EFFICACY OF A CHEMOTHERAPEUTIC REGIMEN FOR GASTROINTESTINAL CANCERS USING ANTIBODIES SPECIFIC FOR THYMIDYLATE SYNTHASE

This application claims the benefit of U.S. Provisional Application No. 60/007,285, filed Dec. 1, 1995, the disclosure of which is incorporated by reference.

BACKGROUND OF THE INVENTION

Gastric adenocarcinoma is characterized by an extremely virulent behavior and for which the mortality approximates the incidence (see, Alexander, et al. *CANCER OF THE STOMACH IN CANCER: PRINCIPLES AND PRACTICE OF ONCOLOGY*, DeVita, et al. (Eds.), J. B. Lippincott Co., Philadelphia, Pa., p. 818–848 (1993)). The vast majority of patients with gastric cancer are diagnosed with advanced stage disease and even after "curative" gastrectomy, most will die from recurrent disease. Recently, there has been increasing interest in the use of neoadjuvant or primary chemotherapy, frequently using fluoropyrimidine-based combination chemotherapy, in an attempt to increase resectability and improve survival for patients with locally advanced gastric cancer. Neoadjuvant chemotherapeutic treatment provides an early opportunity to assess individual patient response using the in situ primary tumor. Overall response rates in studies using neoadjuvant 5-fluorouracil (5-FU) based regimens in locally advanced gastric cancer range from 24 to 45% (see, Ajani, et al., *Cancer* 68:1501–1506 (1991); Leichman, et al., *J Clin Oncol* 10:1933–1942 (1992); and Ajani, et al., *Proc ASCO* 11:165 (1992)). Therefore, at least half of all patients treated in this setting are being subjected to unnecessary toxicity and delay in operation with no therapeutic benefit. Strategies that would accurately predict tumor responsiveness to 5-FU therapy would provide an opportunity to selectively treat patients most likely to benefit from treatment and avoid unnecessary toxicity in those who would not.

The fluoropyrimidines are an important group of antineoplastic agents used widely in the treatment of gastrointestinal as well as other tumors. An important mechanism of 5-FU cytotoxicity is through the inhibition of thymidylate synthase (TS), the enzyme that catalyzes the methylation of 2'-deoxyuridine-5'-monophosphate (dUMP) to 2'-deoxythymidine-5'-monophosphate (dTMP), an essential step in DNA biosynthesis. The level of TS within an experimental tumor has been shown to correlate with 5-FU sensitivity; further, the acute overexpression of TS after 5-FU exposure is associated with resistance to the cytotoxic effects of the drug (Spears, et al., *Cancer Res* 42:450–456 (1982); Keyomars, et al., *J Biol Chem* 263:14402–14409 (1988); Berger, et al., *Mol Pharmacol* 28:461–467 (1985); Clark, et al., *Cancer Treat Rep* 71:261–265 (1987); and Swain, et al., *J Clin Oncol* 7:890–899 (1989)). Recently, TS monoclonal antibodies have been developed and characterized that are highly specific and sensitive ($K_d$ range 0.3–11.0). One of these antibodies, TS106, can detect femtomolar concentrations of cytosolic free (Mr 36,000) and complexed (Mr 38,000) TS enzyme by Western immunoblot analysis (see Johnston, et al., *Cancer Res* 51:6668–6676 (1991) and Johnston, et al., *Cancer Res* 52:4306–4312 (1992)).

We have conducted a study of neoadjuvant 5-FU, leucovorin, and interferon-α followed by resection and consolidation therapy in 22 patients with locally advanced gastric adenocarcinoma. Tumor specimens were obtained endoscopically in 13 patients prior to treatment and during the second or third day of cycle 2 for TS protein quantification and to assess the relationship between clinical response of the primary tumor and patient survival with free, total, or complexed TS protein expression before and after exposure to 5-FU.

SUMMARY OF THE INVENTION

The present invention provides a method for determining whether a chemotherapeutic treatment is appropriate for patients afflicted with gastrointestinal cancers, comprising;
 (a) obtaining a solid tumor tissue sample from the patient;
 (b) measuring a thymidylate synthase expression level in the tissue sample; and
 (c) comparing the thymidylate synthase expression level with a group of standard tumor tissue samples, the standards having known thymidylate synthase expression levels and known responses to the chemotherapeutic treatment, to determine if that chemotherapeutic treatment is appropriate for the patient.

DETAILED DESCRIPTION OF THE INVENTION

Abbreviations

Figure 1:
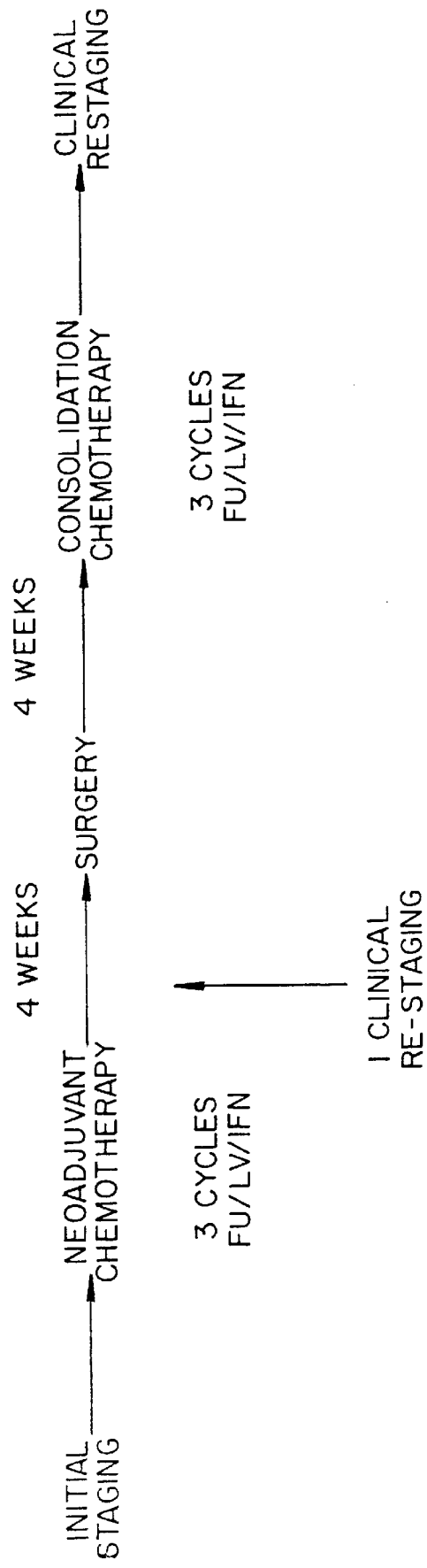
FIG. 1 shows a treatment schema for patients receiving neoadjuvant chemotherapy and resection for locally advanced gastric and gastroesophageal adenocarcinoma.

Abbreviations used herein have the following meanings: ECOG, Eastern Cooperative Oncology Group; LV, leucovorin; 5-FU, 5-fluorouracil; IFN α-2a, interferon α-2a; SGOT, serum glutamoyl transferase; TS, thymidylate synthase; VP-16, etoposide.

Description of the Embodiments

As noted in the Background section above, there has been considerable interest in using neoadjuvant therapy for gastrointestinal cancers in an effort to improve outcome. Others have reported results in 34 patients with laparotomy proven unresectable gastric adenocarcinoma who were treated with up to five cycles of neoadjuvant chemotherapy, surgery, and consolidation chemotherapy. In that study, the overall response rate was 70% and the clinical complete response rate was 21% (see Wikle, et al., *J. Clin. Oncol.* 7:1318–1326 (1989)). Although this study demonstrated the feasibility of this approach for patients with locally advanced gastric cancer, subsequent studies evaluating the etoposide, doxorubicin, cisplatin (EAP) regimen reported lower response rates and substantially higher toxicity (see Kelsen, et al., *J. Clin. Oncol.* 10:541–548 (1992) and Lerner, et al., *J. Clin. Oncol.* 10:536–540 (1992)). The partial response rate in our study of 38% is comparable to other neoadjuvant trials using 5-FU based therapy in gastric carcinoma. Ajani reported a 24% partial response rate following two preoperative cycles of etoposide, 5-FU, and cisplatin, and Leichman reported a 45% response rate after two preoperative cycles of 5-FU, LV, and cisplatin (see, Ajani, et al., *Cancer* 68:1501–1506 (1991) and Leichman, et al., *J. Clin. Oncol.* 10:1933–1942 (1992)).

The resectability rates in the current and latter two neoadjuvant trials were 65%, 72%, and 76%, respectively. Despite very thorough clinical staging, therefore, at least one in four patients will have occult metastatic peritoneal disease. Kang has reported initial results of a random assignment trial of neoadjuvant chemotherapy using 5-FU, cisplatin, and VP-16 for two or three cycles versus surgery alone (Kang, et al., *Proc. ASCO* 11:173 (1992)). The data suggest that neoadjuvant chemotherapy may be effective in reducing local tumor stage and increasing resectability of locally advanced gastric carcinoma. However, the use of two to three cycles of primary chemotherapy followed by a preplanned resection may not represent the optimal treatment approach for patients with clinically occult peritoneal metastases. To this end, the use of endoscopic ultrasound or diagnostic laparoscopy may become increasingly important in the initial staging and selection of patients for neoadjuvant therapy. In our study, unresectability even in the face of a partial response of the primary tumor to neoadjuvant chemotherapy was associated with a median survival of only six to seven months.

The ability to relate response and outcome based on TS protein expression in the primary tumor prior to or early in the course of treatment provides an opportunity to select patients who will be most likely to benefit from 5-FU based therapy and offer alternative regimens to those who will not. As the Examples below demonstrate, quantification of TS protein expression in untreated primary gastric tumors can be carried out using the TS 106 antibody and these expression levels may be associated with response to 5-FU based therapy. It is also demonstrated that tumors with low levels of free TS after exposure to 5-FU tend to respond; moreover, tumors with greater than 80% of the TS bound as ternary complex also have a trend toward being responsive to 5-FU based therapies. No patient with less than 80% of TS complexed after exposure to 5-FU responded to treatment. Overall and in the subset of patients in whom TS levels in tumor were assessed, patients who demonstrated a response to 5-FU therapy had a longer survival than those who did not. These findings have broad applicability for selecting patients with gastrointestinal cancers for 5-FU therapy in the neoadjuvant, adjuvant, or advanced disease setting. Patients can be selected for 5-FU based therapy based upon the sensitivity of the tumor as assessed by free or total TS quantification prior to and complexed TS after a short exposure to 5-FU.

Accordingly, the present invention provides a method for determining whether a particular chemotherapeutic treatment is appropriate for patients afflicted with gastrointestinal cancers, comprising;

(a) obtaining a solid tumor tissue sample from the patient;

(b) measuring a thymidylate synthase expression level in the tissue sample; and (c) comparing the thymidylate synthase expression level with a group of standard tumor tissue samples, the standards having known thymidylate synthase expression levels and known responses to the chemotherapeutic treatment, to determine if that chemotherapeutic treatment is appropriate for the patient.

A number of distinct gastrointestinal cancers can be evaluated using the present methods including rectal cancer, gastric cancer, gastroesophageal cancer and colon cancer. Although each of these cancers have distinct etiologies, it has been surprisingly discovered that TS expression levels are a common phenomenon indicative of prognosis and response to chemotherapy.

The expression of TS has been found to be an important independent prognosticator of disease-free survival and survival in patients with rectal cancer (see, Johnston, et al., *J. Clin. Oncol.* 12:2640–2647 (1994), incorporated herein by reference). In this study, the level of TS expression remained prognostic for both disease-free survival ($P<0.01$) and survival ($P<0.05$) independent of Dukes' stage and other pathologic characteristics examined.

For patients with primary gastric cancer, pretreatment TS levels was found to correlate with response to 5-FU/LV/cisplatin therapy. More particularly, those tumors with high levels of TS protein and TS gene expression tended to be unresponsive to chemotherapy, whereas tumor with low TS protein and gene expression had more responsive disease (see, Johnston, et al., *Cancer Res.* 55:1407–1412 (Apr. 1, 1995), incorporated herein by reference).

Gastroesophageal cancer and locally advanced gastric cancer represent another group of cancers which have been evaluated for TS levels relative to response to chemotherapy. Briefly, a response to neoadjuvant fluorouracil-based therapy was found to be associated with decreased levels of total thymidylate synthase before therapy and free thymidylate synthase after exposure to fluorouracil (see, Alexander, et al., *The Cancer Journal* 1:49–55 (May/June 1995), incorporated herein by reference).

Yet another type of gastrointestinal cancer which can be evaluated by the present inventive method is colon cancer. While colon and rectal cancers are often referred to collectively as colorectal cancers, each has a distinct etiology (see, *THE MERCK MANUAL*, 15th ed., Merck & Co., pp. 818–820 (1987)).

For methods involving each of the cancers above, a solid tumor tissue sample is obtained from a patient. Typically, the tissue sample is obtained by conventional techniques known to those of skill in the art for obtaining biopsy samples. Preferably, the tumor tissue samples are obtained by endoscopic biopsy.

The tissue which is isolated can be used directly, frozen, or it can be embedded in, for example, paraffin and stored for future use. Preferably, the tissue is frozen and stored at temperatures of −20° C. to about −80° C. The term "embedded" refers to a sample that has been infiltrated with a material to provide mechanical support and thereby reduce sample deformation during processes such as sectioning (preparing thin slices for viewing using a microscope). Embedding materials include waxes, such as paraffin wax, epoxies, gelatin, methacrylate, nitrocellulose, various polymers and the like. The term "non-embedded" refers to a sample that is not embedded, and was not previously embedded. When a tissue sample is embedded in, for example, paraffin, for future use, it will preferably be in sections of about 6 micron thickness. Upon removal from storage, the paraffin-embedded tissue sections will be deparaffinized using a relatively non-polar aprotic organic solvent such as xylene, and then rehydrated using graded alcohols followed by phosphate-buffered saline (PBS). Other suitable solvents for removing the embedding support include aliphatic or aromatic hydrocarbon solvents such as toluene, heptanes, octanes, benzene, acetone and acetonitrile.

Following the isolation of tissue samples, thymidylate synthase expression levels are measured in the tissue samples. A variety of methods are available and known to those of skill in the art for measuring TS in a sample. For example, protein levels can be determined by substrate interactions using either a labeled or unlabeled substrate, or by contacting the tissue sample with an antibody specific for thymidylate synthase. In one group of embodiments, the tissue is homogenized in a lysis buffer and centrifuged. The total amount of protein obtained can be quantified and the total protein then separated into component proteins using known methods. Quantification of individual proteins which are present can also be carried out by standard methods. In particularly preferred embodiments, the thymidylate synthase expression levels are determined by contacting the sample or homogenate with an antibody which binds specifically to TS and whose complex can be readily measured.

Antibodies which are specific for TS have been described. See, Johnston, et al., *Cancer Res.* 51:6668–6676 (1991) and Johnston, et al., *Cancer Res.* 52:4306–4312 (1992). Briefly, hybridomas, for example, murine hybridomas, that produce monoclonal antibodies that are immunoreactive with the enzyme thymidylate synthase can be prepared and selected for as described in the Examples that follow. For example, mice (i.e. balb/c mice) can be immunized with the thymidylate protein by intraperitoneal injection. After sufficient time has passed to allow for an immune response, the mice can be sacrificed and the spleen cells obtained and fused, advantageously, with myeloma cells, using techniques well known in the art. The resulting fused cells, hybridomas, are then grown in a selective medium, and the surviving cells grown in such medium using limiting dilution conditions. After cloning and recloning, hybridomas can be isolated that secrete antibodies (for example, of the IgG or IgM class) directed to the target protein, thymidylate synthase, which has a molecular weight of 36,000 daltons.

Hybridomas that secrete antibodies used in the present invention have been deposited with the American Type Culture Collection, and have been assigned the ATCC No. HB-12497, deposited on Mar. 26, 1998 at the American Type Culture Collection (ATCC), 10801 University Blvd., Manassas, Va. 20110. See also, Example/and U.S. application Ser. No. 07/690,841, filed Apr. 24, 1991 and incorporated herein by reference.

Additionally, fragments of the TS-specific monoclonal antibodies, such as Fab or F(ab$^1$)$_2$ can also be used in the present invention. The antibody fragments can be obtained by conventional techniques, for example, by digestion of the antibody using papain or pepsin.

The above-specified examples of the monoclonal antibodies of the present invention are of the IgG and IgM classes, and are obtained from a murine source, however, this is not meant to be a limitation. Other antibodies which are functionally equivalent thereto (that is, capable of specific binding to the above-described TS antigens) are also useful in the present inventive method, whether from a murine source, or other mammal, including human, or combinations thereof. Likewise, use of antibodies of other classes such as IgA, IgE, etc., and isotypes within the classes, is also within the intended scope of the invention.

Isolation and purification of the monoclonal antibodies can be accomplished using various conventional methods, which free monoclonal antibodies from other proteins and contaminants (see, for example, Goding, in *MONOCLONAL ANTIBODIES: PRINCIPALS AND PRACTICE*, Chapter 4, 1986). Preferably, the monoclonal antibodies used in the present invention are able to detect TS in fresh frozen human tumor tissue and paraffin-embedded tissues. Most preferably, the antibody used is the TS 106 antibody described in Johnston, et al., *Cancer Res.* 52:4306–4312 (1992).

The methods of contacting antibodies with the tissue sample (or protein isolates) and determining levels of thymidylate synthase expression can be carried out using standard procedures, including immunoassays which qualitatively and quantitatively analyze the target protein. A general overview of the applicable technology can be found in Harlow and Lane, *Antibodies: A Laboratory Manual*, Cold Spring Harbor Pubs., N.Y. (1988). Either monoclonal or polyclonal antibodies specific for the target protein can be used in various immunoassays. Such assays include, in addition to the Western blots discussed above, ELISA, competitive immunoassays, radioimmunoassays, indirect immunofluorescent assays and the like. In a particularly preferred embodiment, a Western blot technique is used with quantitation by densitometry scanning.

Once the expression levels of TS have been determined in the patient of interest, the levels can be compared with the expression levels from a study cohort, such as that described in Example 2, below, and projections can be made as to the patient's potential for response to a particular chemotherapeutic regimen. As seen in the Examples below, patients having a low tumor TS enzyme level have better responses to neoadjuvant chemotherapy comprising 5-fluorouracil, while those having high (relative) TS enzyme levels have a lesser response to neoadjuvant therapy with 5-fluorouracil. For patients already receiving neoadjuvant therapy comprising 5-FU, a high TS level during the cycle of chemotherapy indicates potential for a lower response to postoperative chemotherapy involving 5-FU regimens.

The importance of the TS enzyme level as a mechanism of drug resistance is indicated by studies demonstrating that acute induction of TS protein as well as stable amplification of TS may be associated with 5-FU resistance in human breast and colon cancer cell lines (Spears, et al., *Cancer Res.* 42:450–456 (1982); Washtein, *Mol. Pharmacol.* 25:171–177 (1984); Chu, et al., *Cancer Res.* 50:5834–40 (1990); Keyomarsi, et al., *J. Biol. Chem.* 263:14402–14409 (1988); Scanlon, et al., *Proc. Natl. Acad. Sci. USA* 85:650–653 (1988); Bradford, *Anal. Biochem.* 72:248–254 (1976); and Hsu, et al., *J. Histochem. Cytochem.* 29:577–585 (1981)). The clinical relevance of acute TS indication has been suggested by an in vivo study carried out on tumor biopsy samples obtained from patients with breast carcinoma that documented a 2- to 6-fold increase in TS 24 hours post-fluorouracil therapy swain (see, Lippman, et al., *J. Clin. Oncol.* 7:890–896 (1989)). These in vivo and in vitro studies suggest that the ability of a tumor to overexpress TS in response to cytotoxic agents is important in the clinical development of tumor resistance.

Until now the measurement of TS levels in human tissue has been carried out by using the radiolabeled FdUMP binding assay (Lockshin, et al., *Biochem. Pharmacol.* 30:247–257 (1981) and Lockshin, et al., *J. Biol. Chem.* 254:12285–12288 (1979)). This assay is performed on a cytosolic extract wherein relatively large quantities of tissue are required and the cellular specificity is lost. The biochemical study assay cannot discriminate between areas of the tumor with differing morphologies, nor can it measure TS on a cell-to-cell basis, and, as tissues and cell preparations are a composite of a heterogenous population, any measurement of TS enzyme is confounded by the degree of contamination by cells other than those of interest. In comparison to the biochemical assay, the availability of a quantitative immunohistochemical assay to measure TS in human cells and tissues is advantageous in the examination of cells in tissue sections. Such an assay allows TS measurement in primary and metastatic tumor samples on a cell-by-cell basis, and facilitates detailed correlations between the level of TS and various clinical and morphological parameters. This information can be of value in patient selection for 5-FU treatment. In addition to TS quantitation in tissues and cells, the antibodies used in the present invention will permit accurate studies of TS production and its regulation by drugs such as 5-FU and methotrexate and biologicals such as the interferons, both in vitro and in vivo. The ability of antibodies to recognize and distinguish native and complexed protein will help provide information about stability of the TS-FdUMP-folate complex and its modulation by exogenous folates.

The invention also relates to a diagnostic kit for detecting the presence of thymidylate synthase, which, in one embodiment, comprise kits such as those described in co-pending U.S. application Ser. No. 07/690,841, incorporated herein by reference.

The following examples are offered solely for the purposes of illustration, and are intended neither to limit nor to define the invention.

EXAMPLES

Complete details for evaluation of rectal cancer can be found in Johnston, et al., *J. Clin. Oncol.* 12(No.12, December):2640–2647 (1994), incorporated herein by reference. Complete details for the evaluation of gastric and gastroesophageal cancers can be found in Johnston, et al., *Cancer Res.* 55:1407–1412 (Apr. 1, 1995) and in Alexander, et al., *The Cancer Journal* 1:49–55 (May/June 1995), the contents of both being incorporated herein by reference.

Example 1

This example illustrates the development and selection of hybridomas which produce monoclonal antibodies specific for thymidylate synthase.

Recombinant thymidylate synthase protein was a kind gift from Dr. D. Santi (University of California). Polyethylene glycol was purchased from J. T. Baker. Pristan was purchased from Aldrich Chemical Co. (Milwaukee, Wis., USA). Peroxidase labeled affinity purified goat antimouse immunoglobulins were purchased from (Kirkegaard and Perry Laboratories, Md., USA). [6-$^3$H] 5 Fdump (18 ci/mmol) was purchased from Moravek Biochemicals (Brea, Calif., USA). $^{14}$C-Methionine was purchased from NEN (Boston, Mass., USA). 96 well Immulon Plates were purchased from Dynatech (Chantilly, Va., USA). A.B.C. Immunoperoxidase kits were purchased from Vector Laboratories (Burlingame, Calif., USA). All other chemicals were obtained from Sigma or NIH supply.

1.1 Immunization Fusion and Cloning

Five female balb/c mice (10 weeks old) were injected intraperitoneally with recombinant human thymidylate synthase (r TS) 10 µg per mouse. The r TS peptide had been emulsified in Freund's complete adjuvant. The mice were subsequently boosted twice with r TS 10 µg/mouse at 21 day intervals. A mouse with high reactivity ($\geq$ 1/100,000 by ELISA) was chosen and injected with r TS 10 µg in 0.5 mL phosphate buffer saline (PBS) 4 days prior to fusion. Spleen cells (1×10$^8$) from the immunized mouse were fused with 2×10$^7$ P3×63 Ag 8 variant 653 myeloma cells by using 50% (v/v) polyethylene glycol 3350 (J. T. Baker Chemical Co.) as a fusing agent. The fusion procedure of Galfre and Milstein was used (Galfre et al., *Nature* 266:550 (1977)). The fused cells were plated onto 96 well plates and screened for monoclonal antibody production by ELISA starting on day 28 post fusion. The ELISA-positive hybridomas were cloned and recloned three times at 1, 10 and 50 cells per 96-well plates on feeder cells. The resultant stable colonies were expanded into 25 CM$_2$ Falcon Flasks. In this fusion 412 hybridomas resulted from plating of fused cells into 768 wells (53%) ELISA positive clones were detected in 114/412 (27%) wells and 38 of these were positive by subsequent western blot assays. The ELISA positive hybridomas were cloned and recloned by limiting dilution techniques. Seven stable hybridomas were produced which secreted antibodies to thymidylate synthesis. These were identified as TS 102, TS 105, TS 106, TS 109, TS 110, TS 111A and TS 111B.

1.2 Preparation and Purification of Ascitic Fluid

The mice were injected intraperitoneally with 0.5 mL of Pristan (Aldrich Chemical Co.) and 10–14 days later inoculated with 1×10$^6$ hybridoma cells per mouse. The ascitic fluid was collected at 2–3 day intervals until the animal was sacrificed. The ascitic fluid was purified by precipitation with 40% ammonium sulphate and high pressure liquid chromatography (Liang, et al., *Biochem. Biophys. Res. Commun.* 128:171–178 (1985)). Isotypic analysis using immunodiffusion techniques indicated that 4 cell lines produced antibodies of the IgG class, and 1 cell line produced antibodies of the IgM class. The class and subclass of the monoclonal immunoglobulins produced were determined by Ouchterlony analysis with antisera specific for µ chains and for IgG and IgM subclasses (Ouchterlony, in *HANDBOOK OF EXPERIMENTAL IMMUNOLOGY*, Weir D. M. (ed.), Oxford and Edinburgh: Blackwell 1976, pp. 655–707). Antibodies TS 106, TS 109, TS 110 and TS 111A belonged to the IgG1 class, while antibody TS 111B belonged to the IgM class.

1.3 Iodination of Recombinant Human TS Protein $^{125}$I-rhTS was prepared using the purified rhTS protein (EC 2.1.1.45). The soluble lactoperoxidase technique was used to label the rhTS with $^{125}$I (FLPC for Monoclonal Antibody Purification (Pharmacia brochure)). The labeled protein was separated from unreacted Na $^{125}$I by passing the iodination mixture through a SEPHADEX® G-25 column, equilibrated and eluted with a buffer containing 0.01 M PBS, pH 7.4, 0.15 M NaCl and 0.1% BSA.

1.4 ELISA

An Immulon II 96-well plate was coated with 50 µL of thymidylate synthase (1 µg/mL) in coating buffer (0.015 M NaHCO$_3$) overnight at 4° C. The wells were then washed thoroughly with PBS/TWEEN® (1 N PBS, 0.1% Azide 0.05% TWEEN®) and incubated with 100 µL of bovine serum albumen 5 mg/mL at room temperature for 1 hour. After washing three times with PBS/TWEEN®, 50 µL of hybridoma supernatant was added and incubated at room temperature for 2 hours. The unbound antibody was then washed off with three further washes of PBS/TWEEN® and 50 µL of alkaline phosphatase conjugated antimouse antibodies were added for 4 hours. The wells were then washed three times in PBS/TWEEN® and 50 µL of substrate solution containing (p-nitrophenyl phosphate (PNP) 40 mg in 20 mL of 100 mM NaHCO$_3$ and 10 mg MgCl$_2$, pH 8.0) was added to each well. The substrate gave a greenish yellow color and the optical density of the reaction was assessed at 405 nm in a microelisa autoreader (Dynatech). Determination of positive hybridomas cultures was based on signals >0.5 units above background.

Example 2

This example illustrates the correlation between thymidylate synthase expression levels and a patient's response to a therapeutic regimen containing 5-fluorouracil.

2.1 Patient Population

From September 1990 to May 1993, 22 patients with locally advanced measurable stage III or IV (AJCC, 1988) gastric or gastroesophageal adenocarcinoma ($T_{3-4}$, $N_{0-2}$, $M_0$) were accrued onto a Phase II study approved by the Institutional Review Board at the NCI. All patients were initially staged with endoscopy, CAT scan of the chest, abdomen and pelvis, upper GI contrast study, and bone scan if clinically indicated or there was an elevation in alkaline phosphatase. All patients gave written informed consent and were surgical candidates based upon clinical extent of disease and medical risks. Other major eligibility criteria included a serum bilirubin $\leq 2.0$ mg/di, SGOT $\leq 127$ U/L, creatinine $\leq 2.0$ mg/dl, ECOG performance status 0–2, absolute granulocyte count (AGC) $\leq 2,000/mm^2$, and platelet count $\leq 100,000/mm^2$.

2.2 Treatment Plan

The treatment regimen is shown in FIG. 1. The protocol originally included cisplatin given by continuous IV infusion on days 2–6 at a dose of 20 mg/m²/d. Because of prohibitive toxicity despite dose reductions in the first 3 patients, the protocol was amended to exclude cisplatin in subsequent patients. Patients received three 21 day cycles of preoperative human interferon α-2a (Roferon, Hoffman-LaRoche, Nutley, N.J.), 5 million units/m² subcutaneously on day 1 through 7. Calcium leucovorin (Ben Venue Laboratories, Bedford, Ohio), 500 mg/m² and 5-FU, 370 mg/m² were administered intravenously on days 2 through 6. LV was given by IV infusion over 30 minutes followed 1 hour later by 5-FU. LV and IFN alfa-2a were supplied by the Division of Cancer Treatment, NCI (Bethesda, Md.). Patients were given ice orally as local cryotherapy to decrease mucositis. Prior to initial treatment, endoscopic biopsy of the primary gastric tumor was obtained and immediately frozen at −200° C. A repeat surveillance endoscopy was also performed on day 3 to 5 of cycle two; in 13 patients tumor biopsy samples were obtained prior to the daily dose of chemotherapy and immediately frozen as above for subsequent TS determination. Three to four weeks after cycle three of chemotherapy, patients were restaged and underwent surgical resection. Patients rendered grossly free of tumor received three cycles of postoperative chemotherapy starting approximately four weeks after surgery. Patients that were unresectable or had gross residual disease after resection were offered alternative treatment. All patients had regular follow-up at three to six month intervals.

2.3 Western Blot Analysis and TS Quantification

Gastric tumor biopsy samples were taken from patients at the time of endoscopy, pre- and during chemotherapy, and were immediately frozen and were stored at −80° C. until processed. Each tissue sample was then placed in 100 μL of lysis buffer (300 mM NaCl, 50 mM Tris pH 7.4, 1% TRITON® X-100) with protease inhibitors (0.1% BSA, 0.1% Chymotrypsin) and homogenized immediately using a tissue homogenizer from Tekman (Cincinnati, Ohio, USA). The lysates were centrifuged at 14,000 rpm for 15 minutes and the supernatant was separated from the tissue. Protein was measured by the method described in Bradford, M. *Anal Biochem* 72:248–254 (1976).

An equal amount of protein (200 μg) from the tissue lysates was resolved by polyacrylamide gel electrophoresis using 12.5% acrylamide, according to the method of Laemmli, U. K., *Nature* 227:680–685 (1970). The gels were transferred onto a nitrocellulose membrane in transfer buffer (48 mM Tris, 39 mM glycine, 0.5 M EDTA in 20% methanol) for 2 hours. The nitrocellulose blots were then incubated at room temperature with blocking solution (blotto: 5% Carnation nonfat milk, 10 mM Tris, 0.01% Thimerosal) for 45 minutes. After washing with PBS-TWEEN® (PBS with 0.1% TWEEN® 20), primary antibody (TS 106, ascitic fluid, 1:100 in blotto) was applied for 90 minutes. After four washes with PBS-TWEEN® and two washes with PBS-TWEEN® and two washes with blotto, secondary antibody (goat anti-mouse horseradish peroxidase, Bio-Rad, 1:2000 in blotto) was applied for one hour. After another four washes with PBS-TWEEN®, the chemoluminescent substrate (luminol, plus enhancer, according to the ECL method of Amersham) was applied for one minute. Blots were then air-dried, covered by a plastic foil and exposed to film (Kodak, X-OMATAR®) for five minutes. Densitometry scanning of the film was performed using a Hewlett Packard Scan Jet Plus and analyzed using an image analysis software program (NIH IMAGE v.1.38; provided by Wayne Rasband, NIMH, NIH (Bethesda, Md., USA)). A TS score in arbitrary units (au) was developed by densitometry scanning. The densitometric measurements were made in a blinded fashion to the clinical status of each patient.

1.4 Statistical Analysis

Comparisons of free, total, complexed and bound TS pre- and during treatment between responders and non-responders were made using the Wilcoxon rank sum text. The Kaplan-Meier method was used to estimate the probability of survival from the date of treatment until date of death or last follow-up. Differences in cycle length before and after surgery were compared using a paired student's t-test. All p-values are two-sided.

1.5 Clinical Outcome

There were 22 patients entered on protocol of which 21 are evaluable for response and follow-up (Table 1). One patient developed grade 3 cardiac toxicity (angina) on cycle one of chemotherapy and was removed from the study. Chemotherapy was administered primarily on an outpatient basis; grade 3–4 clinical and laboratory toxicities are shown in Table 2. Fifteen of 21 patients received postoperative chemotherapy. Six patients were not treated because of progressive disease (two), occult metastatic disease identified at operation (three), or toxicity from chemotherapy (one). In general, preoperative chemotherapy was better tolerated than postoperative therapy (mean cycle length [days,d]; cycle one pre-op: 24 d, cycle four post-op: 30 d; $p_2$=0.008).

TABLE 1

Patient and Clinical Profile

| | |
|---|---|
| Men:Women | 17:5 |
| Age range (years) | 41–77 |
| ECOG Performance States | 0:20 |
| | 1:2 |
| Location of Primary Tumor | number (percent) |
| Body/antrum | 5 (23) |
| Cardia/GE junction | 17 (77) |
| Operations performed | number |
| Distal subtotal gastrectomy | 3 |
| Total gastrectomy | 2 |
| Total gastrectomy with enbloc organ resection | 3 |
| Proximal subtotal gastrectomy | 1 |
| Esophagogastrectomy | 9 |
| No resection | 4 |

Responses to induction chemotherapy were assessed immediately prior to planned resection and are summarized in Table 3. A partial response was defined as a 50% or greater reduction in the product of the perpendicular diameters of the primary lesion. In the context of neoadjuvant therapy, we considered a minor response (25–49% reduction) identified on preresection staging performed approximately two weeks after cycle three as biologically significant and justification for continuing consolidation therapy after resection. The types of surgical procedures performed are listed in Table 1. Three of 20 patients who had asymptomatic primary tumors did not have a resection at laparotomy because of clinically occult metastatic disease (one) or peritoneal disease (two) identified prior to or at operation. All resections were done with an R-2 lymphadenectomy. There was no operative mortality; however, there were five complications in four patients including anastomotic leak (one), abscess (two), fascial dehiscence (one), and wound infection (one). Thirteen of 20 patients (65%) who underwent exploration were rendered free of disease whereas seven patients had palliative or no resection because of residual liver (two) or peritoneal metastases (five). Median potential follow-up is 24 months with 11 of 21 dead of disease.

TABLE 2

Grade III and IV Toxicity*

| | Toxicity grade (%) | |
|---|---|---|
| | III | IV |
| Laboratory | | |
| Platelets | 1(4.5) | 2(9) |
| Leukocyte | 4(18) | 1(4.5) |
| Granulocyte | 1(18) | 5(23) |
| Bilirubin | 1(4.5) | 1(4.5) |
| SGOT | 1(4.5) | 0 |
| SGPT | 2(9) | 0 |
| Clinical | | |
| Stomatitis | 5(23) | 2(9) |
| Diarrhea | 3(14) | 0 |
| Nausea/Vomiting | 3(14) | 0 |
| Rash | 0 | 1(4.5) |
| Neuro-cortical | 0 | 1(4.5) |
| Chest pain | 1(4.5) | 0 |
| Abdominal pain | 1(4.5) | 0 |
| Blurred vision | 1(4.5) | 0 |

*NCI Common Toxicity Criteria

1.6 TS Analysis

Figure 2:
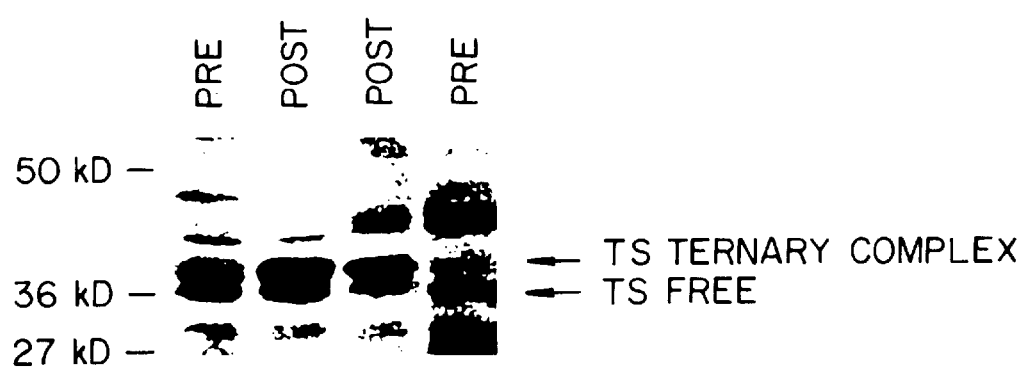
FIG. 2 shows a Western blot demonstrating free ($M_r$ 36,000) and complexed ($M_r$ 38,000) TS bands pre- and post-5FU exposure in a representative responder and nonresponder. The left two lanes show high free TS protein expression pre and post-treatment in a nonresponder. Right two lanes show a lower level of TS protein expression pre and post-treatment and a very high percentage of complexed TS in a responder.
Figure 3:
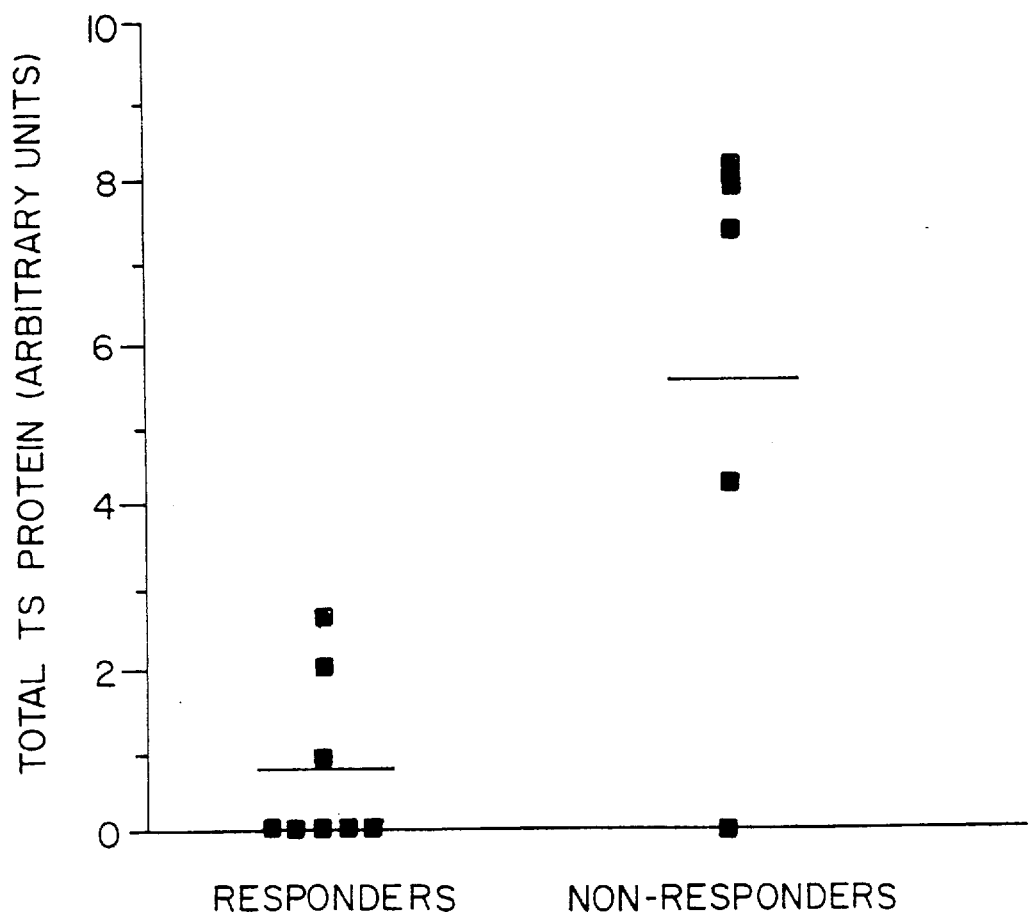
FIG. 3 shows a correlation of TS protein expression in initial gastric tumor biopsies and response to neoadjuvant 5-FU, LV, and IFN ($P_2$=0.031)
Figure 4A:
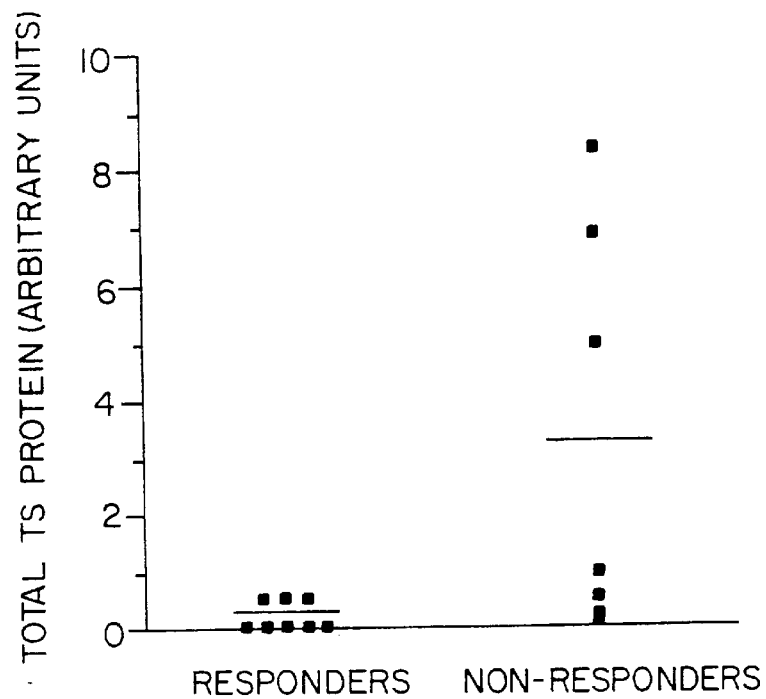
FIG. 4 shows a correlation of free TS (FIG. 4A) and percent complexed TS (FIG. 4B) after 5-FU exposure and response to therapy (free TS: $p_2$=0.019, percent complexed TS: $p_2$=0.056).
Figure 4B:
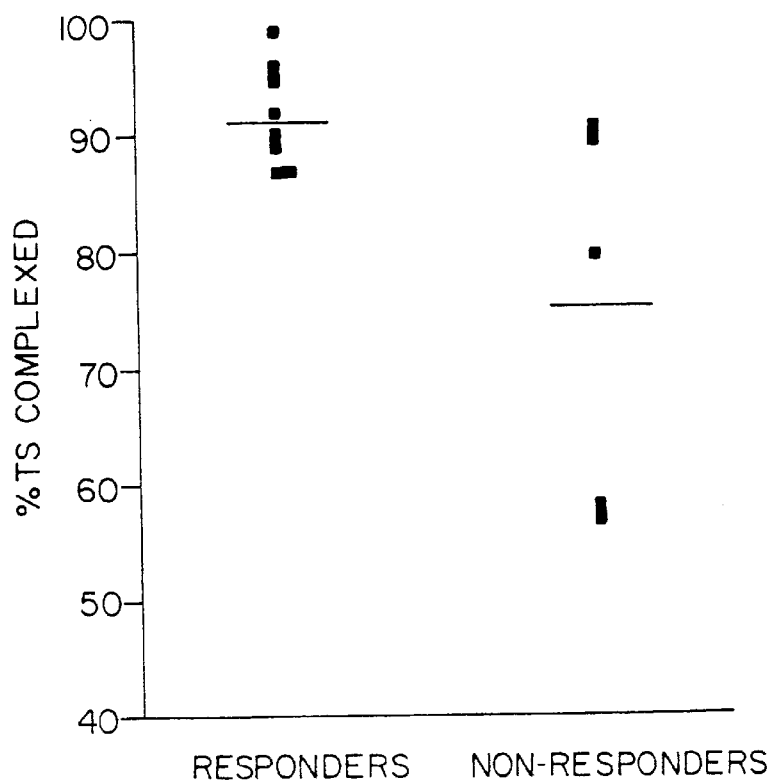

Thirteen patients had paired tumor samples obtained prior to treatment and 48 hours after starting the second cycle of 5-FU/LV/IFN. Eight of these 13 patients had a response to therapy. Using the TS106 antibody and Western immunoblotting, we measured TS total protein ($TS_T$) pre- and post chemotherapy and TS free ($TS_F$), TS ternary complex ($TS_B$), and the ratio of $TS_B/TS_T$ post chemotherapy in gastric biopsy samples (FIG. 2). The level of TS protein expression pre- and post chemotherapy was significantly associated with response to 5-FU/LV/IFN. Patients whose tumors were responding to therapy had much lower baseline levels (mean±SEM) of $TS_T$ (0.7±0.4 au) compared to non-responders (5.5±1.6 au, p=0.03) (FIG. 3, Table 4). The amount of free unbound TS protein ($TS_F$) post chemotherapy was significantly lower in responders than non-responders (0.3±0.1 au vs 3.4±1.7 au, p=0.02) (FIG. 4, Table 4). The percentage bound $TS_B/TS_T$ percentage of 91.8% compared to 75.6% in those with nonresponsive disease (p=0.06) (FIG. 4, Table 4). Of note, one patient with very high levels of baseline TS who had 90% of his TS in the form of TS ternary complex $TS_B$ demonstrated stabilization of disease for several cycles prior to developing progressive disease. In contrast, two other patients with similar high levels of baseline TS protein who had 55–60% of their tumor TS in the form of ternary complex $TS_B$ had progressive disease on therapy. Thus, both total TS protein content prior to therapy and the amount of free unbound TS after 5-FU/LV/IFN are associated with response to TS directed therapy.

TABLE 3

Response Summary*

| | n = 21 (%) |
|---|---|
| Complete Response | 0 |
| Partial Response | 8(38) |
| Minor Response** | 5(24) |
| Stable Disease | 6(29) |
| Progressive Disease | 2(9) |

*Response of primary tumor after three cycles of FU, LV, IFN.
**25–49 % tumor reduction

TABLE 4

Thymidylate Synthase Expression
Correlation With 5-Fluorouracil Response

| TS Parameter | 5-Fluorouracil Exposure | Response[a] | N | TS Expression[b] | $P_2$[c] |
|---|---|---|---|---|---|
| Total ($TS_T$) | Pre | None | 5 | 5.5 ± 1.6 | 0.031 |
| | | MR, PR | 8 | 0.7 ± 0.34 | |
| Total ($TS_T$) | Post | None | 5 | 10.2 ± 3.5 | 0.16 |
| | | MR, PR | 8 | 3.1 ± 0.4 | |
| Free ($TS_F$) | Post | None | 5 | 3.4 ± 1.7 | 0.019 |
| | | MR, PR | 8 | 0.3 ± 0.1 | |
| Complexed ($TS_B$) | Post | None | 5 | 6.8 ± 1.9 | 0.164 |
| | | MR, PR | 8 | 2.8 ± 0.34 | |
| Bound Fraction ($TS_B/TS_T$) | Post | None | 5 | 75.6 ± 7.4 | 0.056 |
| | | MR, PR | 8 | 91.9 ± 1.7 | |

[a]MR, minor response; PR, partial response
[b]Thymidylate synthase (TS) values are expressed as mean SEM
[c]$P_2$ values measured by Wilcoxon rank sum test All publications, patents and patent applications mentioned in this specification are herein incorporated by reference into the specification to the same extent as if each individual publication, patent or patent application was specifically and individually indicated to be incorporated herein by reference.

Although the foregoing invention has been described in some detail by way of illustration and example for purposes of clarity of understanding, it will be obvious that certain changes and modifications may be practiced within the scope of the appended claims.

What is claimed is:

1. A method for predicting the efficacy of chemotherapeutic treatment comprising drugs that target thymidylate synthase for patients afflicted with gastrointestinal cancer, said method comprising;
   (a) obtaining a solid tumor tissue sample from said patient, wherein the sample is obtained prior to chemotherapeutic treatment;
   (b) measuring a thymidylate synthase protein level in said tissue sample; and
   (c) comparing said thymidylate synthase protein level with a group of standard tumor tissue samples obtained prior to chemotherapeutic treatment, said standards having known thymidylate synthase protein levels and known responses to said chemotherapeutic treatment, to predict the efficacy of chemotherapeutic treatment comprising drugs that target thymidylate synthase for said patient.

2. A method in accordance with claim 1, wherein said gastrointestinal cancer is a cancer selected from the group consisting of rectal cancer, colon cancer, gastric cancer and gastroesophageal cancer.

3. A method in accordance with claim 1, wherein said gastrointestinal cancer is colon cancer.

4. A method in accordance with claim 1, wherein said gastrointestinal cancer is rectal cancer.

5. A method in accordance with claim 1, wherein said gastrointestinal cancer is gastric cancer.

6. A method in accordance with claim 1, wherein said gastrointestinal cancer is gastroesophageal cancer.

7. A method in accordance with claim 1, wherein said measuring comprises densitometry following contacting said tissue sample or a preparation thereof with an antibody specific for thymidylate synthase.

8. A method in accordance with claim 1, wherein said chemotherapeutic treatment is a neoadjuvant treatment comprising 5-fluorouracil, leucovorin and interferon α-2a.

9. A method in accordance with claim 1, wherein said chemotherapeutic treatment is an adjuvant treatment comprising 5-fluorouracil, leucovorin and interferon α-2a.

10. A method in accordance with claim 7, wherein said antibody is a TS 106 monoclonal antibody, produced by hybridoma ATCC No. HB-12497.

11. A method in accordance with claim 1, wherein measuring the thymidylate synthase protein level comprises measuring the amount of total thymidylate synthase protein in said tissue.

* * * * *

UNITED STATES PATENT AND TRADEMARK OFFICE
CERTIFICATE OF CORRECTION

PATENT NO. : 5,998,151
DATED : December 7, 1999
INVENTOR(S) : Johnston, et al.

It is certified that error appears in the above-identified patent and that said Letters Patent is hereby corrected as shown below:

In claim 8, line 13, --pre-operative-- should be inserted after "neoadjuvant" and before "treatment."

Signed and Sealed this

Fifth Day of September, 2000

Attest:

Q. TODD DICKINSON

*Attesting Officer*     *Director of Patents and Trademarks*